US00PP23776P3

(12) United States Plant Patent
Bagnasco

(10) Patent No.: US PP23,776 P3
(45) Date of Patent: Jul. 30, 2013

(54) FLORIBUNDA ROSE PLANT NAMED 'BAGSTREAM'

(50) Latin Name: *Rosa hybrida*
Varietal Denomination: Bagstream

(75) Inventor: John J. Bagnasco, Fallbrook, CA (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 13/067,868

(22) Filed: Jun. 30, 2011

(65) Prior Publication Data

US 2013/0007932 P1 Jan. 3, 2013

(51) Int. Cl.
*A01H 5/00* (2006.01)

(52) U.S. Cl.
USPC ..... Plt./143

(58) Field of Classification Search
USPC ..... Plt./143, 145, 146
See application file for complete search history.

*Primary Examiner* — Kent L Bell
(74) *Attorney, Agent, or Firm* — Buchanan Ingersoll & Rooney P.C.

(57) ABSTRACT

A new and distinct variety of Floribunda rose plant is provided which forms in abundance on a substantially continuous basis attractive double bright orange blended with yellow blossoms. The vegetation is vigorous and the growth habit is compact and bushy. Attractive ornamental semi-glossy dark green foliage is formed. Good disease resistance to blackspot is exhibited. The new variety is well suited for growing as distinctive ornamentation in smaller gardens and along walkways. The new plant is particularly well suited for growing in West Coast, U.S.A., climates.

1 Drawing Sheet

Botanical/commercial classification: *Rosa hybrida*/Floribunda Rose Plant.

Varietal denomination: cv. Bagstream.

SUMMARY OF THE INVENTION

The new variety of Floribunda rose plant of the present invention was created by artificial pollination carried out during August 2001 at Fallbrook, Calif., U.S.A., wherein two parents were crossed which previously had been studied in the hope that they would contribute the desired characteristics. The female parent (i.e., the seed parent) was the 'Jacsur' variety (U.S. Plant Pat. No. 9,494). The male parent (i.e., the pollen parent) of the new variety was the 'Jacyimp' variety (U.S. Plant Pat. No. 11,882). The parentage of the present invention can be summarized as follows:

'Jacsur'×'Jacyimp'.

The seeds resulting from the above pollination were sown and small plants were obtained which were physically and biologically different from each other. Selective study resulted in the identification of a single plant of the new variety.

It was found that the new variety of Floribunda rose plant of the present invention possesses the following combination of characteristics:

(a) abundantly and substantially continuously forms attractive double bright orange blended with yellow blossoms,
(b) exhibits a compact and bushy growth habit,
(c) forms vigorous vegetation,
(d) forms attractive ornamental dark green foliage with a semi-glossy finish, and
(e) exhibits good resistance to blackspot.

A new rose variety is provided having attractive bright orange blended with yellow blooms, combined with substantially continuous blooming and resistance to blackspot. The new variety is particularly well suited for growing in West Coast, U.S.A., climates.

The new variety well meets the needs of the horticultural industry. It can be grown to advantage as attractive ornamentation in parks, gardens, public areas, and residential landscapes. Accordingly, it is particularly well suited for growing in the landscape. The new variety fits well for growing in smaller gardens and along walkways. The bloom coloration contrasts nicely with the semi-glossy dark green foliage.

The characteristics of the new variety have been found to be homogeneous and stable and are strictly transmissible by asexual propagation at Wasco, Calif., U.S.A., such as budding, grafting, and propagation by the use of cuttings from one generation to another. Accordingly, the new variety can be asexually reproduced in a true-to-type manner.

The new variety has been named 'Bagstream', and will be marketed under the TANGERINE STREAMS trademark.

The new variety can be readily distinguished from its ancestors upon an inspection of the blossoms. More specifically, the 'Jacsur' variety forms primarily light orange blossoms having a lesser number of petals. The 'Jacyimp' variety forms yellow-orange blossoms also having a lesser number of petals. When the new variety is compared to the 'Gingersnap' variety (U.S. Plant Pat. No. 4,330), it is found that the 'Gingersnap' variety forms larger orange blossoms which also display a lesser number of petals.

BRIEF DESCRIPTION OF THE PHOTOGRAPH

The accompanying photograph shows, as nearly true as it is reasonably possible to make the same in a color illustration of this character, typical blossoms of the new variety. The illustrated plant was approximately two years of age and was being grown outdoors on its own roots during June at West Grove, Pa., U.S.A.

DETAILED DESCRIPTION

The chart used in the identification of colors is that of The Royal Horticultural Society (R.H.S. Colour Chart). The description is based on the observation of two-year-old specimens of the new variety during June while grown outdoors on their own roots at West Grove, Pa., U.S.A.

Class: Floribunda Rose.

Plant:

*Height.*—Approximately 3½ feet on average at the end of the growing season.

*Width.*—Approximately 4 feet on average at the end of the growing season.

*Habit.*—Compact, and bushy.

Branches:

*Color.*—Young stems: near Yellow-Green Group 146B with hints of Greyed-Red Group 181A on the side most exposed to the sun. Young branches: Yellow-Green Group 144C. Adult branches: Green Group 138B.

*Texture.*—Young branches: smooth. Adult branches: smooth.

*Thorns.*—Size: on young branches approximately 6 mm in length on average and up to approximately 1 cm in length on average, and approximately 1 mm in diameter on mature branches. Color: Greyed-Purple Group 183B.

Leaves:

*Size.*—Length: commonly approximately 11.5 cm on average for a five-leaflet leaf. Width: commonly approximately 10 cm on average for a five-leaflet leaf.

*Leaflets.*—Number: 3, 5, and 7. Shape: lanceolate with a serrulate margin, rounded base, and acuminate tip. Size: terminal leaflets commonly are approximately 7.5 cm in length and approximately 4.5 cm in width on average, and lower leaflets commonly are approximately 3 cm in length and approximately 1.5 cm in width on average. Texture: the upper surface is smooth and the under surface is mostly smooth with some roughness along the midrib. Overall appearance: dark green in coloration, with a semi-glossy finish. Color (young foliage): on the upper surface commonly near Yellow-Green Group 144B overlaid with Greyed-Red Group 178B, and on the under surface Greyed-Red Group 178B. Color (adult foliage): on the upper surface commonly near Green Group 137A, and on the under surface Green Group 137C.

*Petioles.*—Length: commonly approximately 3 cm on average. Diameter: commonly approximately 1 mm on average. Texture: generally smooth with small flexible thorns on the under surface. Color: commonly near Green Group 143A.

*Petiolules.*—Commonly absent with leaflets being attached at their bases.

*Stipules.*—Length: commonly approximately 3 cm on average. Width: commonly approximately 2 mm on average. Texture: generally smooth. Color: commonly near Green Group 141A.

Inflorescence:

*Number of flowers.*—Commonly approximately 5 blooms per cane at a given time.

*Peduncle.*—Yellow-Green Group 144B, approximately 4.5 cm in length on average and approximately 3 mm in diameter on average.

*Sepals.*—Number: five. Shape: lanceolate overall. Margin: entire. Apex: acute. Upper surface: commonly between Yellow-Green Group 144B and Yellow-Green Group 144C in coloration, somewhat soft in texture, and moderately tomentose. Under surface: commonly between Yellow-Green Group 144A and Yellow-Green Group 144B in coloration, somewhat rough in texture, and hispidulous. Size approximately 2.5 cm in length on average, and commonly approximately 8 mm in width at the base.

*Buds.*—Shape: rounded to ovoid. Length: approximately 1.5 cm on average. Diameter: commonly approximately 1.5 cm on average. Color: mostly Yellow-Orange Group 15C commonly with streaks of Red Group 46A and Red Group 47A.

*Flower.*—Form: double. Diameter: approximately 7 cm on average. Height: approximately 5 cm on average when open. Color: Upper surface: bright orange, commonly Orange-Red Group 30B, Yellow-Orange Group 14B at the point of attachment, and near Orange-Red Group 32C at the apex and margins. Under surface of inner petals: Yellow-Orange Group 23C, and near Yellow Group 7B at the point of attachment. Under surface of outer petals: Orange Group 24B, Yellow Group 7B at the point of attachment, and near Red Group 47C at the apex. Fragrance: none noticeable. Petal shape: broadly obovate. Petal number: approximately 50 on average. Petal length: commonly approximately 4.5 cm on average. Petal width: commonly approximately 3.7 cm on average. Petal apex: rounded and reflexed. Petal texture: smooth on upper and under surfaces. Petal drop: very good, with the petals commonly dropping cleanly and freely. Stamen number: approximately 80 on average. Anthers: approximately 2 mm in length on average, approximately 1 mm in width on average, and Yellow-Orange Group 17C in coloration. Filaments: Yellow-Orange Group 17C in coloration, and commonly approximately 3 to 5 mm in length. Pollen: commonly present in a sparse quantity and near Yellow-Orange Group 17A in coloration. Pistils: separate and free, and commonly approximately 70 in number on average. Styles: commonly approximately 1 cm in length on average and near Greyed-Yellow Group 160C in coloration. Stigma: commonly approximately 1 mm in diameter on average and near Yellow-Orange Group 15C in coloration. Receptacle: substantially spherical in shape, approximately 1 cm in length on average, approximately 8 mm in width on average, smooth in texture, and commonly near Yellow-Green Group 144B in coloration. Receptacle: achenes stand on the bottom and wall.

Development:

*Vegetation.*—Vigorous and strong.

*Blossoming.*—Abundant and substantially continuous.

*Resistance to diseases.*—Good with respect to blackspot, rust and mildew.

*Propensity to form hips/seeds.*—Spare.

Plants of the new 'Bagstream' variety have not been observed under all possible environmental conditions to date. Accordingly, it is possible that the phenotypic expression may vary somewhat with changes in light intensity and duration, cultural practices, and other environmental conditions.

I claim:

1. A new and distinct variety of Floribunda rose plant characterized by the following combination of characteristics:

(a) abundantly and substantially continuously forms attractive double bright orange blended with yellow blossoms, (b) exhibits a compact and bushy growth habit, (c) forms vigorous vegetation, (d) forms attractive ornamental dark green foliage with a semi-glossy finish, and (e) exhibits good resistance to blackspot;

substantially as herein shown and described.

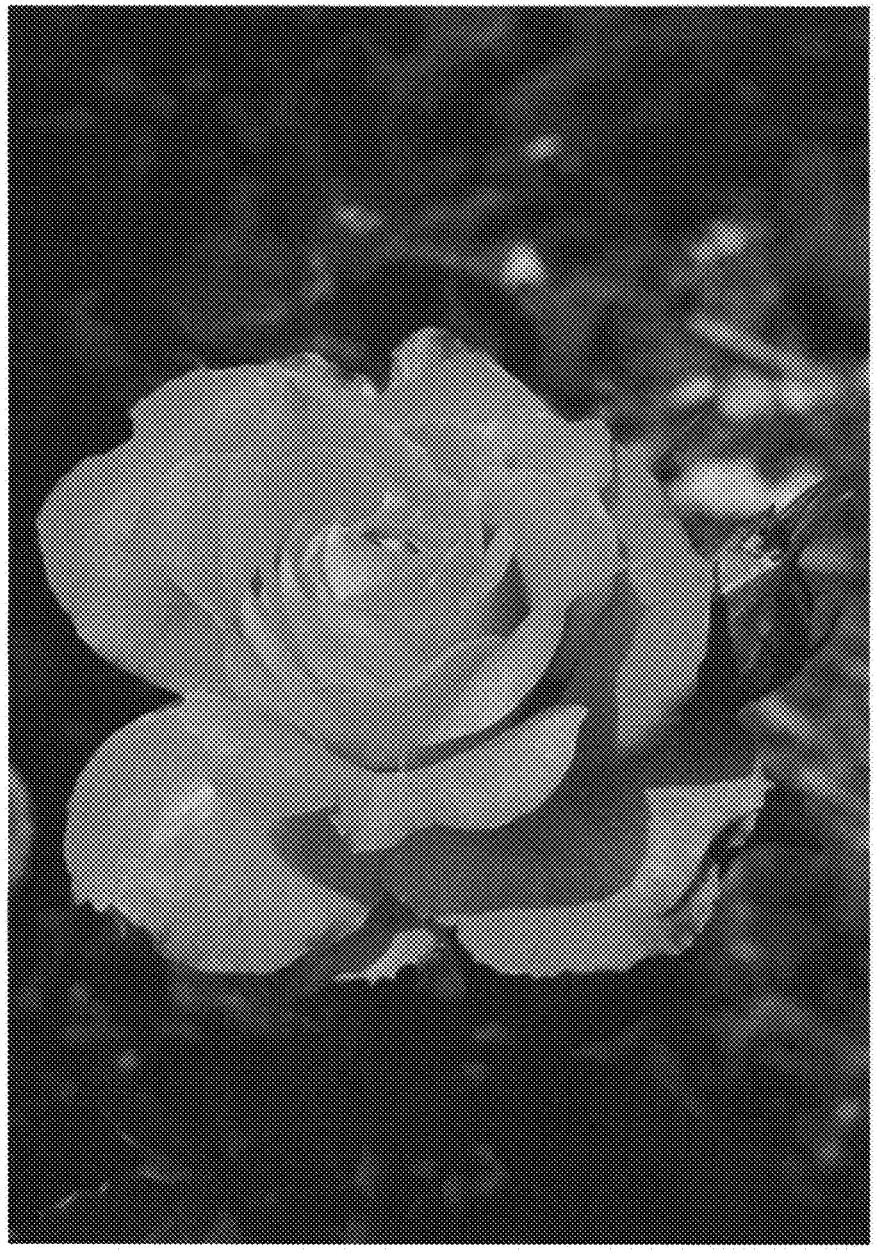

* * * * *